United States Patent
Burren et al.

(10) Patent No.: US 12,083,314 B2
(45) Date of Patent: Sep. 10, 2024

(54) INJECTION OR INFUSION DEVICE COMPRISING AN IMPROVED RELEASE LINER

(71) Applicant: Ypsomed AG, Burgdorf (CH)

(72) Inventors: Stefan Burren, Schwarzenburg (CH); Mario Bernhard, Burgdorf (CH); Bernhard Bigler, Niederönz (CH); Susanne Schenker, Aarwangen (CH); Andres Mellenberger, Koppigen (CH); Christian Schrul, Burgdorf (CH); Markus Tschirren, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 951 days.

(21) Appl. No.: 17/016,742

(22) Filed: Sep. 10, 2020

(65) Prior Publication Data
US 2020/0405950 A1     Dec. 31, 2020

Related U.S. Application Data

(63) Continuation of application No. PCT/IB2019/051358, filed on Feb. 20, 2019.

(30) Foreign Application Priority Data

Mar. 15, 2018   (EP) ..................... 18161873
Mar. 27, 2018   (EP) ..................... 18164145
Nov. 22, 2018   (EP) ..................... 18207808

(51) Int. Cl.
*A61M 5/142*     (2006.01)
*A61M 5/162*     (2006.01)
*A61M 5/28*      (2006.01)

(52) U.S. Cl.
CPC ........ *A61M 5/14248* (2013.01); *A61M 5/162* (2013.01); *A61M 5/285* (2013.01); *A61M 2005/14252* (2013.01)

(58) Field of Classification Search
CPC .......... A61M 2205/13; A61M 5/14248; A61M 5/2466; A61M 5/285; A61M 5/2455;
(Continued)

(56) References Cited

U.S. PATENT DOCUMENTS 3,260,147 A     7/1966 Farabee
3,260,149 A     7/1966 Deaver
(Continued)

FOREIGN PATENT DOCUMENTS

EP     2512552 B1      2/2015
EP     3260147 A1 *   12/2017    ........ A61M 5/14248
(Continued)

OTHER PUBLICATIONS

International Preliminary Report on Patentability Received for International Application No. PCT/IB2019/052421, mailed on Sep. 29, 2020, 6 pages.

(Continued)

*Primary Examiner* — Jason E Flick
*Assistant Examiner* — Adam J. Cermak
(74) *Attorney, Agent, or Firm* — Dorsey & Whitney LLP (57) ABSTRACT

An injection device configured for attachment to the skin of a patient using an adhesive layer includes a release liner covering the adhesive layer thereby preventing skin attachment. The release liner comprises a sheet of material where a first surface contacts the adhesive layer, and an aperture defining a passage for a film connected to a first sterile barrier film located within the injection device. An end of the film is connected to a second surface of the sheet of material that is opposite to the first surface, and the release liner is covered by a strengthening sheet connected to the second surface and covering the aperture and the end of the film.

20 Claims, 5 Drawing Sheets

(58) Field of Classification Search
CPC .... A61M 2025/0035; A61M 2005/247; A61M 2005/2492; A61M 2039/0686; A61J 1/1406; A61J 1/2024
See application file for complete search history.

(56) References Cited

U.S. PATENT DOCUMENTS

| | | | |
|---|---|---|---|
| 3,260,151 A | 7/1966 | Jones | |
| 3,909,910 A * | 10/1975 | Rowe | F16L 29/00 D24/129 |
| 4,019,512 A * | 4/1977 | Tenczar | A61M 39/14 604/905 |
| 5,019,047 A | 5/1991 | Kriesel | |
| 6,382,442 B1 * | 5/2002 | Thibault | A61J 1/1406 215/325 |
| 6,679,529 B2 | 1/2004 | Johnson et al. | |
| 6,843,782 B2 * | 1/2005 | Gross | A61M 5/50 604/110 |
| 8,315,687 B2 * | 11/2012 | Cross | A61B 5/282 600/509 |
| 9,248,232 B2 * | 2/2016 | Yodfat | A61B 5/14532 |
| 9,427,529 B2 * | 8/2016 | Cabiri | A61M 5/14248 |
| 10,758,721 B2 * | 9/2020 | Sonderegger | A61M 5/158 |
| 2001/0056262 A1 * | 12/2001 | Cabiri | A61M 5/14248 604/180 |
| 2003/0030272 A1 * | 2/2003 | Johnson | F16L 29/00 285/70 |
| 2004/0116866 A1 * | 6/2004 | Gorman | A61M 37/00 604/93.01 |
| 2008/0048436 A1 | 2/2008 | Matkovich et al. | |
| 2009/0095290 A1 | 4/2009 | Cain et al. | |
| 2011/0166512 A1 | 7/2011 | Both et al. | |
| 2012/0316506 A1 * | 12/2012 | Sonderegger | A61M 5/1626 604/180 |
| 2014/0008366 A1 | 1/2014 | Genosar | |
| 2015/0105691 A1 * | 4/2015 | Hadvary | A61B 17/3403 604/110 |
| 2015/0217058 A1 | 8/2015 | Hooven et al. | |
| 2015/0320990 A1 * | 11/2015 | Burton | A61M 5/1454 604/173 |
| 2016/0089056 A1 | 3/2016 | Limaye et al. | |
| 2016/0199568 A1 | 7/2016 | Mcnall et al. | |
| 2016/0220798 A1 * | 8/2016 | Netzel | A61M 5/14244 |
| 2016/0256665 A1 | 9/2016 | Doshi et al. | |
| 2016/0310663 A1 * | 10/2016 | Dantsker | A61M 5/31571 |
| 2016/0310665 A1 * | 10/2016 | Hwang | C09J 7/21 |
| 2017/0020423 A1 * | 1/2017 | Fujita | A61M 5/14248 |
| 2017/0259015 A1 | 9/2017 | Caspers | |
| 2018/0353704 A1 * | 12/2018 | Helmer | A61M 5/2466 |
| 2019/0240417 A1 * | 8/2019 | Hostettler | A61M 5/31511 |
| 2019/0274924 A1 * | 9/2019 | Barmaimon | A61L 2/07 |
| 2019/0374707 A1 * | 12/2019 | Damestani | A61M 5/24 |
| 2020/0001068 A1 * | 1/2020 | Donze | A61M 5/5086 |
| 2020/0297917 A1 * | 9/2020 | Helmer | A61M 5/001 |
| 2020/0316290 A1 * | 10/2020 | Bourelle | A61M 5/31 |
| 2020/0397984 A1 | 12/2020 | Reed et al. | |
| 2020/0405950 A1 | 12/2020 | Burren et al. | |
| 2020/0405951 A1 | 12/2020 | Burren et al. | |
| 2020/0405952 A1 | 12/2020 | Rytz et al. | |
| 2021/0001048 A1 | 1/2021 | Schrul et al. | |
| 2021/0030949 A1 | 2/2021 | Damiano et al. | |
| 2021/0038805 A1 | 2/2021 | Goldstein | |
| 2021/0093849 A1 | 4/2021 | Stumpe et al. | |
| 2021/0128844 A1 | 5/2021 | Boyaval et al. | |
| 2021/0170095 A1 | 6/2021 | Diperna et al. | |
| 2021/0260279 A1 * | 8/2021 | Boyaval | A61M 5/1626 |

FOREIGN PATENT DOCUMENTS

| | | | |
|---|---|---|---|
| EP | 3260149 A1 * | 12/2017 | ........ A61M 5/14248 |
| EP | 3260151 A1 * | 12/2017 | ........ A61M 5/14248 |
| EP | 3052166 B1 | 4/2019 | |
| EP | 3539591 A1 | 9/2019 | |
| EP | 3539592 A1 | 9/2019 | |
| EP | 3539596 A1 | 9/2019 | |
| EP | 3545997 A1 | 10/2019 | |
| EP | 3582825 A1 | 12/2019 | |
| EP | 3697475 A1 | 8/2020 | |
| WO | 9959665 A1 | 11/1999 | |
| WO | WO-2006067217 A2 * | 6/2006 | .......... A61B 5/4839 |
| WO | 2008068695 A1 | 6/2008 | |
| WO | 2011015659 A1 | 2/2011 | |
| WO | 2011064780 A2 | 6/2011 | |
| WO | 2011075099 A1 | 6/2011 | |
| WO | 2017089271 A1 | 6/2017 | |
| WO | 2017089286 A1 | 6/2017 | |
| WO | WO-2017219155 A1 * | 12/2017 | .............. A61M 5/46 |
| WO | 2018151890 A1 | 8/2018 | |
| WO | 2019175688 A1 | 9/2019 | |
| WO | 2019175689 A1 | 9/2019 | |
| WO | 2019175690 A1 | 9/2019 | |
| WO | 2019186375 A1 | 10/2019 | |

OTHER PUBLICATIONS

Extended European Search Report received for European patent application No. 18164145.7, issued on Nov. 12, 2018, 6 page.
International Search Report and Written Opinion received for International Application No. PCT/IB2019/051357 mailed on May 7, 2019, 12 pages.
International Search Report and Written Opinion received for International Application No. PCT/IB2019/051358, mailed on May 15, 2019, 9 pages.
International Search Report and Written Opinion received for International Application No. PCT/IB2019/051359, mailed on May 15, 2019, 10 pages.
International Search Report and Written Opinion received for International Application No. PCT/IB2019/052421, mailed on Aug. 6, 2019, 10 pages.
International Preliminary Report on Patentability received for International Application No. PCT/IB2019/051357, mailed on Sep. 15, 2020.
International Preliminary Report on Patentability received for International Application No. PCT/IB2019/051358, mailed on Sep. 15, 2020.
International Preliminary Report on Patentability received for International Application No. PCT/IB2019/051359, mailed on Sep. 15, 2020.

* cited by examiner

# INJECTION OR INFUSION DEVICE COMPRISING AN IMPROVED RELEASE LINER

RELATED APPLICATIONS

This application is a continuation of International Patent Application No. PCT/IB2019/051358, filed Feb. 20, 2019, entitled "AN INJECTION OR INFUSION DEVICE COMPRISING AN IMPROVED RELEASE LINER," which claims priority European Patent Application No. 18161873.7, filed Mar. 15, 2018, entitled "AN INJECTION OR INFUSION DEVICE COMPRISING AN IMPROVED RELEASE LINER", and European Patent Application No. 18164145.7, filed Mar. 27, 2018, entitled "AN INJECTION OR INFUSION DEVICE COMPRISING AN IMPROVED RELEASE LINER", and European Patent Application No. 18207808.9, filed Nov. 22, 2018, "AN INJECTION OR INFUSION DEVICE COMPRISING AN IMPROVED RELEASE LINER", each of which is incorporated by reference herein, in their entirety and for all purposes.

TECHNICAL FIELD

The current invention relates to an injection device that is configured for attachment to the skin of a patient using an adhesive layer, the injection device comprises a release liner covering the adhesive layer. The release liner has an aperture and is strengthened using a strengthening sheet of material. Additionally a method is presented for application of the strengthening sheet to the release liner.

BACKGROUND

Injection and infusion devices are used for the subcutaneous delivery of liquid medicaments to a patient. Such injection devices are often pen-shaped, having a long axis and are called injection pens. The injection pens comprise a housing, which can hold a dose setting and dose delivery mechanism. The medication is preferably present in a cartridge or in a prefilled syringe. A cartridge is normally attached to the housing of the injection pen using a cartridge holder. The user sets a dose of medication which is subsequently delivered from the cartridge. Such injection pens are used to deliver separate injections and not intended for continuous delivery of a medicament. The needle is attached to the injection pen each time before use and the needle penetrates a septum that is attached to the cartridge.

Infusion devices deliver the medication from the cartridge using a drive mechanism and a control mechanism that controls the advancement of a piston rod that abuts a moveable plunger present in the cartridge containing the medication. The medication is delivered to the patient via a fluid path and an external infusion set comprising a needle for subcutaneous delivery. With such infusion devices both continuous and temporary medicament delivery profiles can be programmed.

A patch device is an example of an infusion device that is attachable to the skin of the patient. Such patch devices do not need an external infusion set for delivery as the needle is directly contained in the patch device and may be inserted into the patient therefrom.

The injection and infusion devices comprise a dose setting mechanism, a delivery mechanism, a needle insertion and retraction mechanism or a needle shield protection system which is connected or connectable to a drive mechanism. The drive mechanism is driven by a power source which supplies energy to the injection or infusion device for executing tasks such as medication delivery, establishing a connection between the fluid path and the cartridge, needle insertion, needle retraction, advancing and/or retracting a piston rod, signaling to the user that the medication is in progress and/or complete, signaling to the user that the device can be removed, powering a processor unit in the device or establishing a wireless connection for data transmission to an external device such as a smart phone. The power source used in such injection or infusion devices can be selected from a wide variety of options such as, but not limited to, a spring (compression, torsional spring, and leaf spring), an electric motor, a battery, pressurized gas or liquid-hydraulic systems and the like. In the injection and infusion devices, several operations need to be arranged in a certain sequence for a correct operation and transmission of power from the energy source to final medicament delivery, for example, by advancing the plunger in the cartridge.

For a patch injection device, the needle must be inserted first, either using a steel needle (also called cannula) or a combination of a steel needle with a soft cannula; subsequently the steel needle must be retracted to leave the soft cannula in the subcutaneous tissue of the patient, followed by delivery of medication. Preferably, the needle, either a soft needle or a steel needle is retracted into the device before the patch device can be removed from the body. Alternatively, the needle is not retracted but a needle shield is extended from the body of the device to protect the needle tip and prevent needle sticks of the patient.

The liquid medicament is produced under sterile conditions and enclosed in a container to maintain the medicament sterile. Such a container can be the above mentioned cartridge or an ampoule, both of which are preferably made of glass. As an alternative plastic containers may be used. The cartridge comprises a barrel having two openings, one opening at the end of a neck portion and a second opening opposite to the neck portion. The opening at the neck portion is normally closed by a penetrable septum that is attached to the neck portion using a crimp. The opposite opening is closed by a plunger and the medicament is enclosed by the barrel between the septum and the plunger. During medication delivery, the plunger in the cartridge is advanced in the cartridge by the drive mechanism. The cartridge is filled with the liquid medicament in a fill finish line, and either the plunger is inserted first into the barrel and the medicament is filled via the neck portion followed by closure using the septum crimped onto the neck portion, or the septum is attached first to the cartridge's neck and the medicament is filled from the opposite opening and finally closed by the plunger. The fill finish is done in a sterile environment. The filled cartridge is normally subjected to a visual inspection to ensure that no particulates are present in the liquid.

The filled cartridge is assembled with an injection or infusion device, preferably a patch device, having a fluid path unit that is used for establishing the connection between a fluid path and the liquid medicament. The fluid path unit comprises a housing or compartment for housing a fluid path in the interior. The fluid path may comprise a needle or spike that can pierce through the septum of the cartridge, a tubing for fluid transfer connecting the needle or spike to a second needle (which is either a soft needle and/or a steel needle) intended for penetrating the skin of the patient. Preferably, during storage there is no connection between the cartridge and the fluid path and just prior to use the connection is established by penetrating the septum of the cartridge with the spike or needle. The interior of the housing or compartment for the fluid path unit is sterilized during manufacturing and remains in a sterile condition during storage. The fluid path unit and the cartridge can be assembled in a sterile environment which may be cumbersome (for example in view of the visual inspection) and expensive or it is assembled in a non-sterile environment such as a clean room. The device comprising the assembly of the fluid path unit and cartridge can be in a sterile packaging during storage which is removed just before use or it is in a non-sterile packaging. In either option, a sterile connection needs to be established between the content of the cartridge and the fluid path in the compartment of the fluid path unit prior to use and this is usually done in a non-sterile environment.

US20160199568 discloses an infusion device with a peristaltic pump. The tubing of the pump is connected to a connector assembly comprising an ampoule with a liquid medicament and a connector for the tubing. Between the ampoule and the connector there are two strips to prevent the liquid passing from the ampoule to the tubing. The ampoule is directly closed by the film and not with a septum, and the connector for the tubing is always connected to the ampoule—there is no spike or needle for establishing the connection between the liquid medicament just prior to use. Removing the strip simultaneously establishes: a) a fluid connection between the cartridge and the tubing, and b) a sterile connection between the ampoule and the tubing. The fact that there is no separate closure for the ampoule reduces the reliability of the fixed connection and it cannot be used for a modular assembly approach; moreover it will be cumbersome to use standard fill-finish procedures and standard components (such as a cartridge closed by a septum) for the device described in US20160199568.

In U.S. Pat. No. 4,019,512, a sterile connection between two connector ends of two ports or tubes is established in a non-sterile environment by removing two strips from the two connector ends. The two strips maintaining the ends of the tubes in a sterile environment during storage and the strips are removed after the two connector ends have been connected. A sterile connection is established between two tubes and not intended or suitable for establishing a connection between a cartridge and a fluid path of an infusion device.

It is an object of the present invention to overcome the above mentioned drawbacks for an injection device that is configured for attachment to the skin of a patient and improve the usability of the device and the reliability of the release liner removal while simultaneously removing one or two sterile barrier films that are connected to the inside of the injection device. It is a further object of the present invention to remove one or two sterile barrier films that are removably connected to the inside of the injection device and additionally remove a further sterile barrier film connected to the outside of the housing of the injection device during removal of the release liner.

These objectives are solved by covering the release liner with a strengthening sheet that adhesively connects to both the surface of the release liner as well as to an end of the sterile barrier film. The strengthening sheet covers and strengthens the aperture in the release liner. This objective is further solved by covering two ends with two sterile barrier films that are removably attached to an inside surface within the device, one film being attached to the passage of the fluid path whereas the other film is removably connected to the cartridge and covering the septum. A further objective is solved by attaching the strengthening sheet to the ends of the sterile barrier films that are releasably connected to the inside of the device and attaching the strengthening sheet to the further sterile barrier film connected to the outside housing of the injection device.

SUMMARY

In priority European Patent Application EP18161873.7 a cartridge is provided that is closed with a septum and therefore steps a) and b) that are mentioned in the background section and occur simultaneously in the prior art are separated from each other. First a sterile connection is established between the fluid path and the standard cartridge and secondly the spike or needle of the fluid path penetrates the septum of the cartridge to establish the fluid connection. The advantage of having a standard cartridge closed by a septum and crimp is that standard production procedures can be used for fill-finish of the cartridge using standard components which increases the reliability of the assembly and the acceptance by pharmaceutical companies. A modular approach can be used, and the cartridge may be filled at a different location than the assembly with the fluid path unit. Another advantage is that the cartridge with the sterile surface on the septum can be assembled with the sterile fluid path unit in a non-sterile environment. The connection shown in US20160199568 must be assembled in a sterile environment.

In priority European Patent application EP18161873.7, the septum of the cartridge is covered by a sterile barrier film and/or a passage inside of the injection device is covered by a sterile barrier film. The films are intended to maintain the surface of the septum in a sterile condition and/or to maintain a fluid path unit enclosed in a compartment having the passage in a sterile condition. The ends of the films extend through a passage in the housing and through a passage in an adhesive layer configured for attaching the device to the skin of the patient. Prior to use, the adhesive layer is covered with a release liner protecting the skin adhesive layer. The ends of the sterile barrier films are connected to the release liner and the two sterile barrier films are removed simultaneously from the septum and the passage, respectively when removing the release liner from the adhesive layer. For a correct attachment of the ends of the sterile barrier films to the release liner, a passage or aperture in the release liner is also required. The sterile barrier films that are attached to the septum and the passage, respectively, of the fluid path, need to extend through the passages in the housing, the adhesive layer and the release liner before the end of the sterile barrier can be attached to the surface of the release liner. A disadvantage of this approach is that the passage in the release liner weakens the liner as corners of the passage may act as stress concentrators upon liner removal. This may lead to tear damage, or in the worst case, only partial removal of the release liner causing discomfort to the patient and potentially prevents the attachment of the device to the patient's skin.

It is an objective of the present invention to provide an injection device which is configured for attachment to the skin of a patient using an adhesive layer. The adhesive layer may be directly attached to the outside surface, for example to the housing of the injection device. The injection device comprises a release liner that covers the adhesive layer and thereby prevents undesired attachment of the injection device to the skin of the patient. The release liner comprises a sheet of material wherein a first surface of the sheet contacts the adhesive layer. The first surface of the sheet may entirely cover the adhesive layer such that the sticky surface is covered by a non-sticky sheet of material. The release liner further comprises an aperture which defines a passage for a film that is connected to a first sterile barrier film which is located within the injection device, such as within the housing of the injection device. The first sterile barrier film may pass through an aperture present in the injection device, such as through an aperture within the housing or through an aperture connecting the inside of the housing to the outside of the housing. An end of the first sterile barrier film may be connected to a second surface of the sheet of material that is opposite to the first surface, i.e., the surface that is not contacting the adhesive layer. The release liner may be covered by a strengthening sheet which is adhesively connected to the second surface of the sheet of material and covering the aperture in the release liner and the end of the film. The end of the film may be connected to the sheet of material forming the release liner, such that the end of the film and therewith also the first sterile barrier film connected thereto can be removed together with the release liner when the liner is removed. This facilitates the formation of a sterile connection within the injection device upon use while maintaining the material behind the sterile barrier film in a sterile condition during storage. The end of the sterile film may be required to pass through the release liner for attachment to the second surface such that an aperture in the sheet of material is required. Upon release of the release liner, the user pulls on the release liner and will pull also on the end of the first sterile barrier film, requiring an additional force leading to local stress concentrations around the aperture in the sheet of material, for example in the corners of the aperture. These stress concentrations may be above the tear strength of the sheet of material and lead to local disruption or tearing of the release liner. For example the release liner can only be partially removed which is not desired as it reduces the reliability of the device during use as proper skin attachment is prevented or increases user complaints as the device cannot be operated. Therefore the strengthening sheet is adhesively attached to the release liner covering at least the aperture in the sheet of material, and thereby strengthening the release liner, thus preventing fracture due to local stresses around the aperture. Additionally the end of the first sterile barrier film may also be covered by the strengthening sheet and thereby strengthens the link between the end of the first sterile barrier film and the release liner, ensuring a safe removal of an intact release liner including the end of the film and the first sterile barrier film connected thereto.

The injection device may have one first sterile barrier film or may have a plurality of first sterile barrier films, each connected to a surface of the inside of the housing. One end of at least one sterile barrier film is connected to the second surface of the sheet of material forming the release liner. The end of a second or third first sterile barrier film may be connected to the second surface of the sheet of material as well. The strengthening sheet of material covers and attaches to one end of at least one first sterile barrier film; however, the strengthening sheet may cover the plurality of ends of the plurality of first sterile barrier films.

The release liner may further comprise a second aperture for a hollow needle in which the end of the hollow needle is configured to be moved from a first position within the injection device to a second position outside the injection device, the second aperture for the hollow needle being covered by a removable second sterile barrier film that is adhesively attached to the strengthening sheet. The second sterile barrier is connected to the strengthening sheet and thus results in removal of the second sterile barrier together with the first sterile film when the release liner is removed. The second sterile barrier film may not be connected or attached to the sheet of material forming the release liner. The effect is that when users remove the release liner, then the first and second sterile barrier films are removed simultaneously in a single step and a sterile connection is established within the device and the insertion needle is uncovered and free for insertion into the skin of the patient and can move from the inside to the outside of the device without penetrating the second sterile barrier film. This increases the usability of the device for the patient, as only a single step is required, namely liner removal.

The first sterile barrier film forms a removable sterile barrier within the injection device covering a passage or an aperture that is located inside of the injection device or inside of the housing that is part of, and encloses the injection device. The removable sterile barrier film may have edges or edge regions that are attached to a housing or a housing part inside the device where the passage is located within the housing or housing part. The edges or edge regions may be attached to the housing section adjacent to the passage or aperture. The attachment or connection between the sterile barrier film and the housing section has a strength, such as a shear strength or peel-off strength, which is below the tear or tensile strength of the sterile barrier film such that the connection between the edges of the film and the housing section adjacent of the passage fails when the release liner is removed. Alternatively, the sterile barrier film or the housing section adjacent from the passage has a locally reduced strength such that either the sterile barrier film or the housing section fail in a controlled manner when the release liner is removed. A removable first sterile barrier film ensures that the film can be removed to open the passage such that, for example, a needle can pass through the passage without penetrating the barrier film and having the risk of needle blockage and particulate formation which decreases the reliability of the device.

The passage or aperture on the inside of the injection device may be part of a sterile compartment enclosing a fluid path comprising a spike or hollow needle configured to be moved within the injection device through the passage into a septum of a cartridge. The sterile compartment may be part of the housing or a housing part of the injection device and the passage or aperture is part of a wall section of the housing or housing part. The passage or aperture is may be oriented perpendicular to the planes forming the first and second surfaces of the release liner when the release liner is attached to the adhesive layer, i.e., perpendicular to a bottom surface of the housing intended to be placed onto the patient's skin. The passage is open when the sterile barrier film is removed and the passage is available for the needle to move through the passage and establish a fluid path connection to the medicament in the cartridge. The spike or hollow needle is driven by an insertion mechanism that may be driven by a spring and the spike or hollow needle may move parallel to the plane of the first and second surfaces of the release liner when attached.

The injection device with the first sterile barrier film forms a removable sterile barrier within the injection device covering a septum of a cartridge, and maintains a surface of the septum in a sterile condition. The surface that is kept in a sterile condition is opposite to the septum's surface contacting the liquid medicament. The injection device may comprise a first sterile barrier film covering a passage or aperture of a sterile compartment with a fluid path as described above and a second first sterile barrier film that covers the septum of the cartridge. It may be advantageous that more than two first sterile barrier films are removably attached within the injection device. The first sterile barrier covering the septum of the cartridge maintains the septum in a sterile condition during storage. The septum covered by the first sterile barrier film may be sterilized as a unit and the barrier film prevents contamination during storage. Just before use, the first sterile barrier films covering the septum and the passage are removed to form a sterile connection between the needle (or spike) and the liquid medicament, thus preventing contamination when the fluid path connection is established upon needle (or spike) insertion through the septum.

The film may be an integral part of the first sterile barrier film, or the film is separate from and connected to the first sterile barrier film forming a pull tab for the first sterile barrier film. When the film is separate from the first sterile barrier film then it may be glued, heat-welded, ultra-sonic welded or attached to the sterile barrier film using a bracket or a clip. The pull tab may be integrated with the sterile barrier film, for example both may be constructed from Tyvek® or another porous film such as paper allowing for gas plasma or ethylene oxide sterilization. Alternatively, a separate pull tab is attached to the sterile barrier film and constructed from a non-porous polymer film such as polyethylene terephthalate (PET), polybutylene terephthalate (PBT), polyethylene (PE), polypropylene (PP) or the like. Alternatively, paper or reinforced or laminated paper may be used. The pull tab may be constructed from a film having a higher bending resistance compared to the first sterile barrier film as it may be folded within the device. For example an elastomeric material may be used.

The end of the film or the end of the pull tab that is connected to the first barrier film is adhesively connected or welded to the second surface of the release liner. The end of the film is arranged through the passage in the release liner prior to connecting to the second surface of the liner. Subsequently the connection of the end of the film or pull tab to the second surface is reinforced using the strengthening sheet. The strengthening sheet may be an adhesive film having an adhesive layer covering the passage in the release liner and the at least one end of the film. A robust connection between the end of the film and the release liner is established ensuring that upon removal of the liner also the end and the removable sterile barrier can be removed from the device in a single step.

The strengthening film covers and adhesively connects to the end of the film of the first sterile barrier film covering the passage of the sterile compartment enclosing the fluid path and/or the strengthening film covers and adhesively connects to the end of the film of the first sterile barrier film covering the septum of the cartridge. Thus, either one or both ends are covered by the strengthening sheet of material. Alternatively two separate strengthening sheets may be applied for each end of both first sterile barrier films. At least one of the two strengthening sheets covers the second aperture for a hollow needle. The strengthening sheet ensures that at least one first sterile barrier film and the removable second sterile barrier film covering the second aperture in the housing are simultaneously removed upon release liner removal.

In embodiments, the strengthening film covers the second sterile barrier film and the end of the film of the first sterile barrier film covering the passage of the sterile compartment enclosing the fluid path. The strengthening sheet covers the second sterile barrier film (covering the hollow insertion needle) and the end of the film covering the fluid path compartment. This facilitates that the strengthening sheet is adhered to the end of the first sterile barrier film covering the fluid path unit and this strengthening sheet can be mounted and adhered to the second surface of the sheet forming the release liner before the cartridge with the sterile barrier film is mounted in a separate step, and possibly at a different time or geographic location. The cartridge is inserted in a separate step and the septum of the cartridge may be covered by a first sterile barrier film. The end of the sterile barrier film covering the septum may be adhered to the second surface of the release liner using a second strengthening sheet or a part of the first strengthening sheet that has not yet been used.

The release liner having two strengthening films adhesively attached to the second surface of the sheet of material forming the release liner may be configured such that one of the two strengthening films covers and adhesively connects to the second sterile barrier film and the end of the film of the first sterile barrier film covering the passage for the sterile compartment enclosing the fluid path.

The release liner may comprise a conductive layer, for example a silver ink layer or a carbon black layer, covering and being part of a signaling sensor, for example a capacitive sensor. The conductive layer may for example electrically shield a part of the capacitive sensor. The conductive layer may be part of, or coated onto the sheet of material forming the release liner or may be part of the sheet of material that strengthens the release liner. The conductive layer may be, for example, applied on the sheet of material and/or onto the strengthening sheet using metal vacuum deposition techniques or printing techniques. The metal may be selected from silver, gold or aluminum. Also a carbon layer may be deposited onto the surface using vacuum deposition or printing techniques. Alternatively, the release liner is constructed from a conductive material such as a sheet of aluminum or a carbon filled plastic material wherein the carbon particles form a percolating network. The conductive layer may be a continuous layer covering the whole release liner or it may be partially covering the release liner. The conductive layer effects electrical shielding of the sensor when the release liner is attached to the device and removal of the liner causes a change in capacitance measured by the sensor and which can be used to detect proper removal of the release liner by enabling electrical signaling to a control unit in the device.

The injection device comprises a housing enclosing a fluid path present in a compartment, and the fluid path comprises a needle for penetrating the septum of the cartridge connected by a tube to a hollow needle for penetrating the skin of a patient. The compartment comprises the passage covered by the removable first sterile film. The fluid path compartment enclosed by the housing may be sterilized while the first removable sterile barrier film is attached to, and cover the passage. For example the first sterile barrier film is constructed of a porous membrane such as Tyvek®, and the fluid path compartment is sterilized using gas plasma or ethylene oxide gas sterilization. Alternatively radiation sterilization techniques may be used such as gamma-radiation, e-beam or X-rays. The housing enclosing the fluid path compartment may include the second aperture for the hollow needle that is intended for penetrating the skin of the patient. The housing enclosing the fluid path compartment may form the main housing, i.e., outer housing of the injection device or it may be an internal housing part. In the latter case at least one outer housing encloses the housing for the fluid path compartment. Each of the housing or housing parts has a passage for the film that is connected to the release liner and the housing or housing parts are configured to guide the film, for example around rounded edges surrounding the passages, pins or protrusions present in the housing to allow for a smooth removal of the film and the first sterile barrier film connected thereto.

The injection device comprises an outer housing enclosing inner housing parts such as the housing for the fluid path compartment. The outer housing comprises an outer surface configured for application of the skin adhesive layer. The outer housing supports subassemblies present in the housing such as the drive mechanism, a control mechanism for controlling the device, and a needle insertion and retraction mechanism. The outer housing may have a cover or closure cap that can be removed for insertion of a cartridge followed by closing the housing using the cover or cap. Such a closure cover or cap may comprise a viewing window for viewing the cartridge and the progress of the injection.

The injection device comprises a cartridge holder for holding a cartridge comprising a fluid medicament sealed in a barrel by a moveable plunger and a pierceable septum covered by the removable first sterile barrier film. The cartridge holder may be part of an internal housing component, for example, the housing forming the sterile compartment for the fluid path, or it may be part of an internal housing holding the drive mechanism. Optionally there may be a separate housing part dedicated to receive the cartridge and that is connectable to the outer housing.

The skin adhesive layer is connected to an outside surface of the housing and may comprise a skin adhesive for adhesion to the skin, a circuit layer comprising an electrically conductive sensor, and an adhesive layer for adhesion to the outside surface of the housing. The electrically conductive sensor of the adhesive layer may be at least partially covered by the conductive layer of the release liner when the release liner is attached to the adhesive layer.

A method for assembling an injection or infusion device that can be attached to the skin using an adhesive layer which is covered by a release liner prior to use is disclosed and involves the steps of: Providing a housing assembly comprising a fluid path comprising a needle that is configured to penetrate the septum and a needle that is configured for insertion into the skin of the patient (e.g., a skin insertion needle). The fluid path is enclosed in a housing part or fluid path compartment having a passage that is covered by a second sterile barrier film thereby maintaining the fluid path in a sterile condition. Guiding an end of the second sterile barrier film through a passage in the housing, the adhesive layer and the release liner. Attaching the end of the second sterile barrier film to the outside surface of the release liner that is not in contact with the skin adhesive layer. Providing a cartridge filled with a medicament and closed with a septum that is attached to the cartridge using a crimp. The surface of the septum is covered by a first sterile barrier film that is connected to the crimp thus maintaining the surface of the septum in a sterile condition. The sterile barrier film comprises an end which ensures that the first sterile barrier film can be removed from the crimp. Insertion of the cartridge into a cartridge holder that is part of the injection device, the cartridge is inserted such that the end of the first sterile barrier film of the cartridge is guided through a passage in the housing, the adhesive layer and the release liner. Attaching the end of the first sterile barrier film to the outside surface of the release liner that is not in contact with the skin adhesive layer. Applying an adhesive sheet of material onto the outside surface of the release liner, thereby at least covering both ends of the first and second sterile barrier films and the passage in the release liner.

Optionally, a second sheet of strengthening material is attached to the outside surface of the release liner before cartridge insertion.

As another option the first sterile barrier film covering the septum is extended by connecting a pull tab thereto which may be constructed from a different material than the first sterile barrier film. The pull tab is attached to the first sterile barrier film prior to the cartridge insertion step.

As a further option, a flip off cap covering the first sterile barrier film and/or the pull tab is attached to the crimp, the flip off-cap is at least partially removed before insertion of the cartridge into the cartridge holder.

BRIEF DESCRIPTION OF THE DRAWINGS

While the invention has been described in detail in the drawings below and foregoing summary, such description is to be considered illustrative or exemplary and not restrictive. Variations to the disclosed embodiments can be understood and effected by those skilled in the art and practicing the claimed invention, from a study of the drawings, the disclosure, and the appended claims.

DETAILED DESCRIPTION

The term "medicament" or "medication" includes any flowable medical formulation suitable for controlled administration through a means such as, for example, a cannula or a hollow needle and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from or harvested by biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

The distal end or distal direction is defined by the direction of the needle configured to penetrate the skin of the patient. For an injection pen this may be the injection needle and the end of the pen holding the needle or being configured to hold the needle is the distal end. For an infusion device the distal end and the distal direction is towards the needle configured to penetrate the skin of the patient, which may be along the axis of the device or tilted or perpendicular to the axis of the device. The distal direction in an infusion device represents the direction in which the medicament flows towards the insertion needle. The proximal direction or end is opposite to the distal direction or end.

Figure 1:
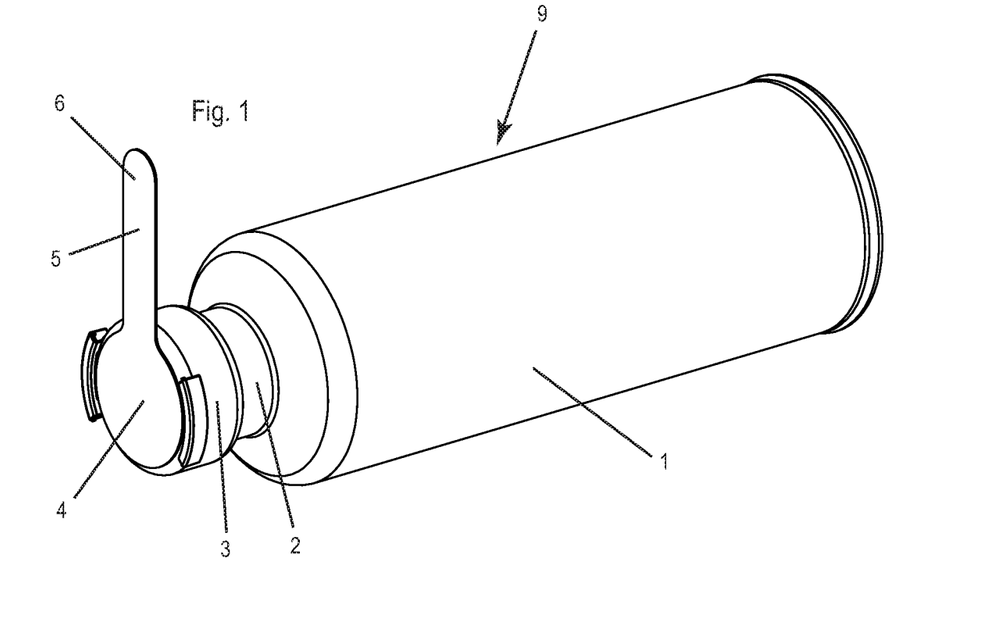
FIG. 1: Cartridge closed by a septum with a crimp, the first sterile barrier film is connected to the crimp thereby covering the septum. The free end of the film is an integral part of the first barrier film.
Figure 2:
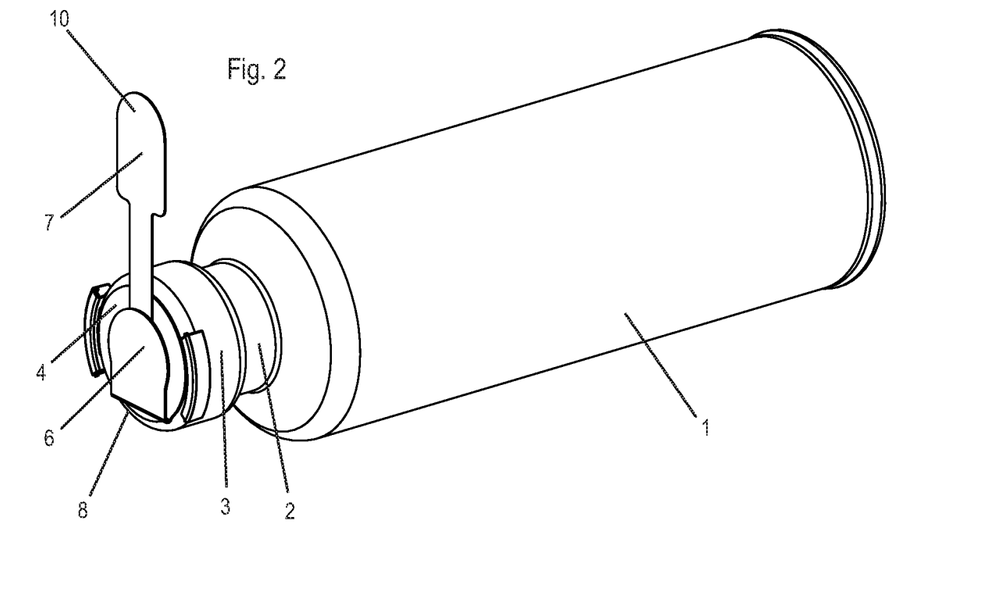
FIG. 2: Cartridge closed by a septum with a crimp, the first sterile barrier film is connected to the crimp thereby covering the septum. The film is a separate film forming a pull tab and is connected to the first barrier film.

Turning to FIG. 1, a cartridge (9) is illustrated and comprises a barrel (1) or ampoule, for instance constructed of glass or from a polymeric material such as polypropylene or cyclo-olefinic polymer (or copolymer). The barrel (1) may be cylindrically shaped and have a narrowed neck (2) closed by a septum (27—FIG. 4) that is connected to the cartridge (9) using a crimp (3). The crimp (3) defines an opening surrounding the septum (27). A first film (5), which may be a flexible film, has been removably attached to the crimp using a first sterile barrier film section (4). An end (6) of the first film (5) is not attached to the crimp and available for attachment to a release liner of the device or to a connector film, as will be discussed herein. FIG. 2 illustrates an alternative embodiment in which the end (6) of the first film is attached to a connector film (7) that is separate from the first film (5). The first film (5) has a U-shaped fold (8) and the connector film (7) is sandwiched between the first sterile barrier film (4) and the end (6) of the first film (5). The connector film (7) has been attached to the first film (5) using adequate attachment means such as gluing or welding. The connector film (7) includes a pull tab (10) for connecting to the release liner. The first barrier film (4) may be a porous film that enables gas sterilization such as gas plasma (hydrogen peroxide) or ethylene oxide sterilization (ETO) to sterilize the septum of the cartridge. Examples are non-woven porous polyethylene or polypropylene films or paper (cellulose) films that may be laminated or coated to enhance or control the adhesive properties.

Figure 3:
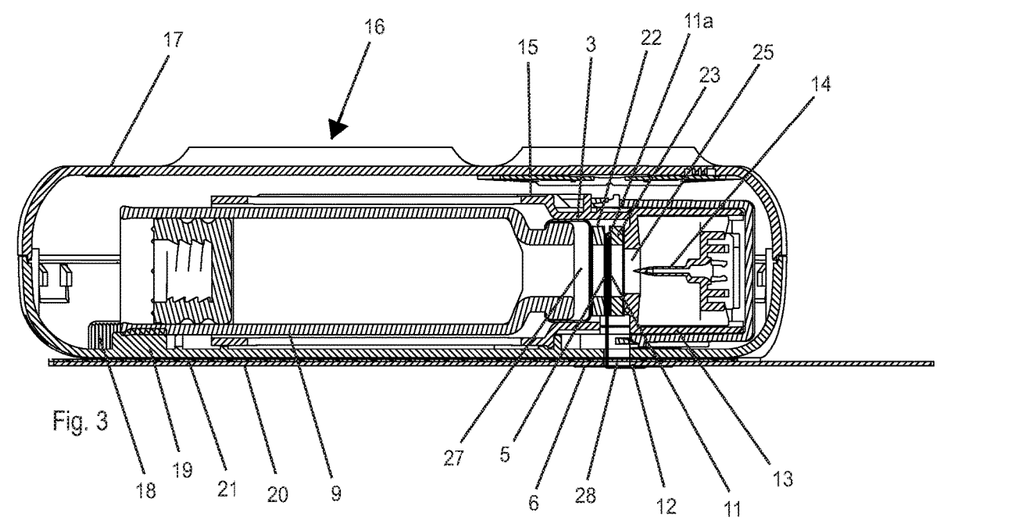
FIG. 3: Longitudinal section of an injection device illustrating the cartridge with a septum covered by a removable barrier film and a passage for a sterile compartment enclosing a needle that is covered by another removable barrier film. The ends of the films are connected to the outer surface of the release liner.
Figure 4:
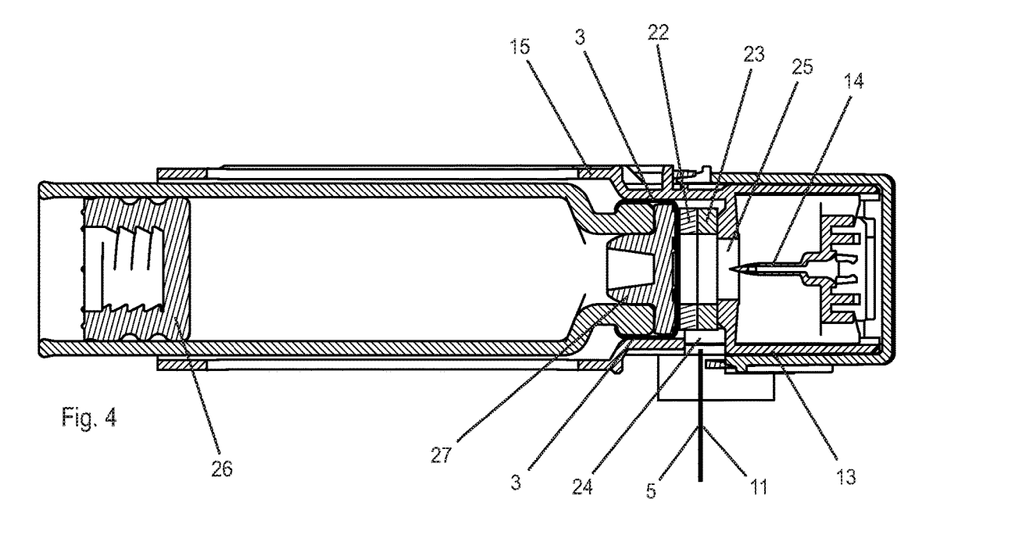
FIG. 4: Detailed view of the assembly of the cartridge and the fluid path unit of FIG. 3 when the release liner is removed.
Figure 5:
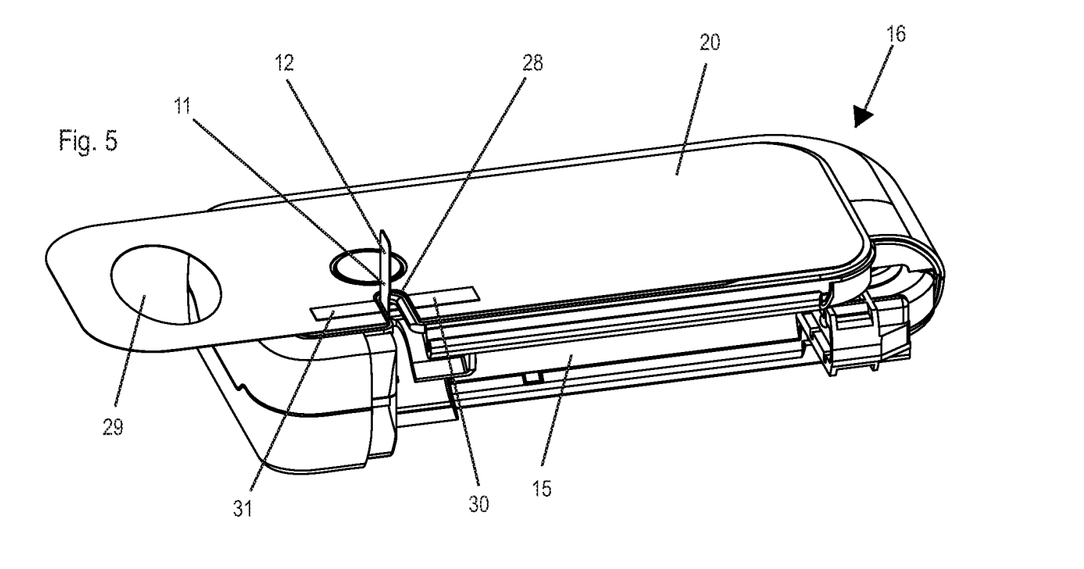
FIG. 5: Injection device during assembly, the film connected to the second sterile barrier film covering the passage of the fluid path compartment passes through the apertures within the housing and the release liner and extends past an exterior of the device.
Figure 6:
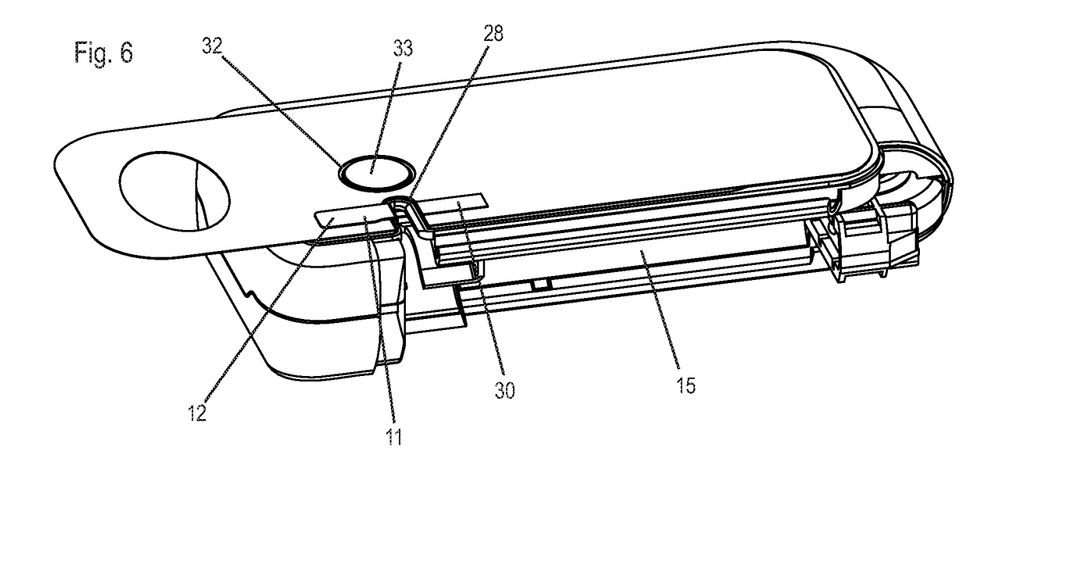
FIG. 6: Injection device during assembly, the end of the film illustrated in FIG. 5 is attached to the outside surface of the release liner at the exterior of the device.
Figure 7:
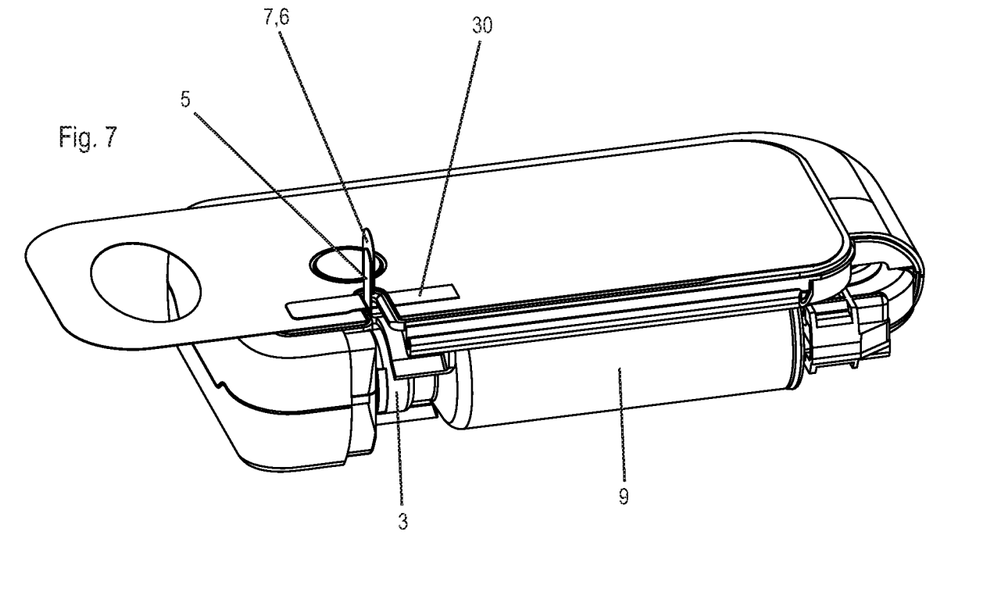
FIG. 7: Injection device during assembly, the cartridge with a sterile barrier film covering the septum (FIGS. 1 and 2) has been inserted into the cartridge holder. The end of the film passes through the apertures in the housing and the release liner and extends past the exterior of the device.

FIG. 3 illustrates a longitudinal section of an injection device (16) showing an assembly of the cartridge (9) inserted into the injection device (16). The injection device (16) may be attached to the skin of the patient using a skin adhesive layer (21) which is covered by a release liner (20). FIG. 4 illustrates a detail view of when the first film (5) and a second film (11) have been removed together with the release liner (20). The function of the second film (11) will be discussed below. In FIG. 4, the cartridge (9) is illustrated with a moveable plunger (26) that can move towards the septum (27) for expelling the medicament. The external housing (17) encloses both the cartridge (9) and a compartment (13) for the fluid path enclosing a needle (14) that is aligned parallel to the longitudinal axis of the cartridge (9). The first and second films (5, 11) are positioned between the fluid path needle (14) and the cartridge (9). The cartridge is positioned within a cartridge holder (15) which, for this example, is part of the compartment (13) for the fluid path. The cartridge (9) is axially fixated in the housing (17) and biased towards the compartment (13) of the fluid path using a ratchet system (18, 19). A ratchet member (18) may be axially guided in the housing (17) after the cartridge (9) has been inserted such that ratchet teeth of the ratchet member (18) engage ratchet teeth of a counter ratchet member (19) axially fixed with respect to the housing (17). The ratchet member (18) engages a proximal rim of the barrel of the cartridge (9) thereby enabling axial fixation of the cartridge in the housing (17) and biasing the cartridge (9) towards the compartment (13) of the fluid path. Alternatively, and instead of the ratchet member, the cartridge is fixed using a ridge or fin on a cover (not shown) that may close the compartment (13) and during closing, the rib or fin may be elastically deformed on the proximal rim of the cartridge (9) thereby fixing the cartridge. The first film (5) is connected to the crimp (3) of the cartridge, which fixes a septum (27) to the neck (2). The first sterile barrier film (4) is an integral part of the first film (5) and is connected to the crimp (3) using a first member (22). The first member (22) may be for example a glue or a double-sided adhesive tape. Optionally the first member (22) is a resilient member such as an O-ring, which may be compressed once the cartridge (9) is fixed using the ratchet system (18, 19). The first sterile barrier film (4) may also be directly heat-welded onto a distal end surface of the crimp (3). The first sterile barrier film (4) is connected to the crimp (3) such that this connection can be released by applying a force to the end (6) of the first film to peel-off the first sterile barrier film (4) from the crimp (3).

The fluid path compartment (13) includes a passage (25) which allows the fluid path needle (14) to move through the passage (25). The passage (25) is covered by a second film (11) and the second barrier film (11a) which is an integral part of the second film (11) is attached to a wall of the fluid path compartment (13) and covering the passage (25), thereby preventing contamination of the fluid path comprising the needle (14). The second barrier film (11a) may be a porous film that enables gas sterilization such as gas plasma (hydrogen peroxide) or ethylene oxide sterilization (ETO) to sterilize the fluid path. The second sterile barrier film (11a) may be connected to the fluid path compartment (13) using a second member (23). The second member (23) may be for example glue or a double-sided adhesive tape. The second member (23) may optionally be a resilient member such as an O-ring which may be compressed once the cartridge (9) is fixed using the ratchet system (18, 19). The second sterile barrier film (11a) may also be directly heat welded onto the wall of the compartment (13) comprising the passage (25). The second sterile barrier film (11a) may be connected to the compartment (13) such that this connection can be released by applying a force to the end (12) of the second film (11) to peel-off the second sterile barrier film (11a) from the compartment (13) such that the passage (25) is free for the fluid path needle (14) to move therethrough.

The first and second films (5, 11) are guided through an aperture (24) in the cartridge holder (15) such that the ends of the first and second films (6, 12) can be guided through an aperture (28) in the release liner (20).

The ends of the films (6, 12) are connected to the outer surface of the release liner (20) such that the first and second films (5, 11) are removed from the crimp (3) respectively passage (25) upon removal of the release liner (20) from the skin adhesive layer (21), see FIG. 4. Optionally, a gap that may exist between the septum (27) and the wall of the fluid path compartment (13) after removing the first and second films (5, 11) may be closed due to the resilience of the connecting members (22, 23) and/or due to the ratchet system (18, 19) which immediately closes the gap. A disadvantage of the assembly illustrated in FIGS. 3 and 4 is that the aperture (28) in the release liner (20) acts as a stress concentrator such that the release liner can easily tear leading to partial removal of the release liner (20). As a consequence, the device cannot be properly attached to the skin of the patient.

An embodiment according to the present invention is illustrated in FIGS. 5 to 9. A bottom view of the injection device (16) is illustrated, e.g., shown upside down, with the release liner (20) covering the skin adhesive layer (21). The release liner (20) includes a cut-out (29) acting as a handle to facilitate the removal of the release liner (20). The release liner (20) includes an aperture (28), which is C-shaped extending inwardly from the side or edge of the release liner (20) to facilitate the insertion of the second film (11) from the side using the end (12) of the second film (11). The outside surface of the release liner (20), i.e., the surface that is not contacting the skin adhesive, comprises a second adhesive spot (31) which may be a double sided adhesive tape. The end of the second film (12) is attached to the outside surface of the release liner (20) using the second adhesive spot (31), see FIG. 6. Alternatively, the second adhesive spot (31) is present at the end (12) of the second film (11). Other attachment means for the end (12) of the second film (11) are, for example, heat welding or ultrasonic welding. In addition, the surfaces that contact to each other may be roughened, etched, blasted, heat treated or plasma treated to enhance the adhesive connection therebetween. Once the end of the second film (12) has been attached to the release liner (20), the cartridge (9) may be inserted into a side of the cartridge holder (15), see FIG. 7. The end (6) of the first film (5) or the pull tab (10) of the connector film (7) may be guided into the C-shaped aperture (28) during cartridge insertion, and the first and second films (5,11) may be arranged parallel to another and contact each other. The end of the first film (6) or the pull tab (7) is attached to the release liner using a first adhesive spot (30), see FIG. 8. The options presented above for attaching the second film (11) to the second adhesive spot (31) equally apply to attachment of the first film (5) to the first adhesive sport (30).

The sequence presented in FIGS. 5 to 8 may also be reversed, i.e., the cartridge (9) may be inserted and the first film (5) is attached to the release liner (20) followed by attaching the second film (11) to the release liner.

Figure 8:
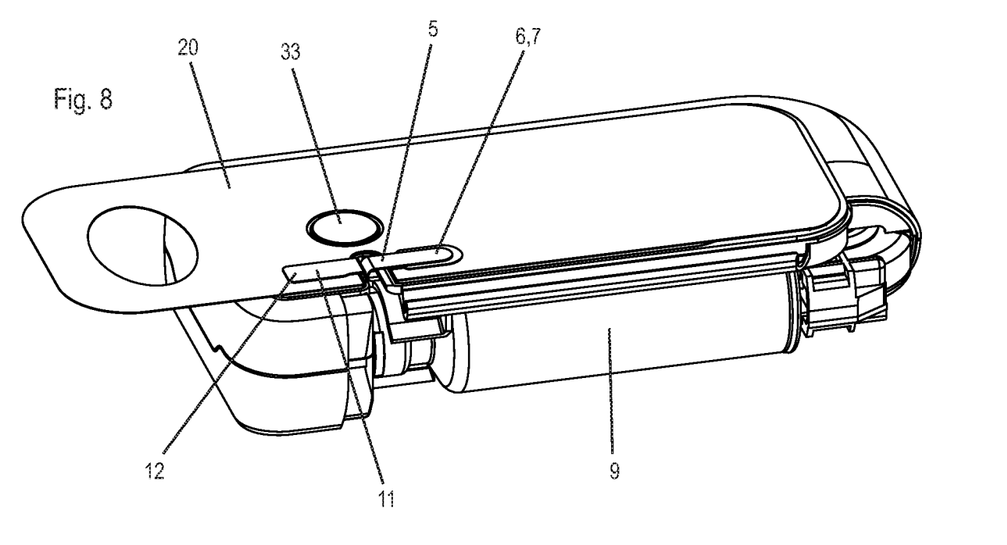
FIG. 8: Injection device according to FIG. 7 during assembly, the end of the film covering the septum is attached to the outside surface of the release liner at the exterior of the device.

The release liner (20) comprises a second aperture (32) that surrounds a third sterile barrier film (33), FIG. 8. The third sterile barrier film (33) is removably connected to the housing (17) of the injection device or to the housing of the fluid path compartment (13). The third sterile barrier film (33) covers a passage in the housing that is available for a hollow, skin piercing needle to move from a first position in the injection device to a second position outside the injection device for penetrating the skin of the patient. The hollow, skin piercing needle may move between the first and second positions perpendicular to a plane of the release liner (20). The third sterile barrier film (33) may be constructed from the same material as the first and second sterile barrier films (4,11a) and allows for gaseous sterilization techniques. The release liner (20) may not be directly connected to the third sterile barrier film (33) but the release liner (20) may surround the third sterile barrier film (33).

Figure 9:
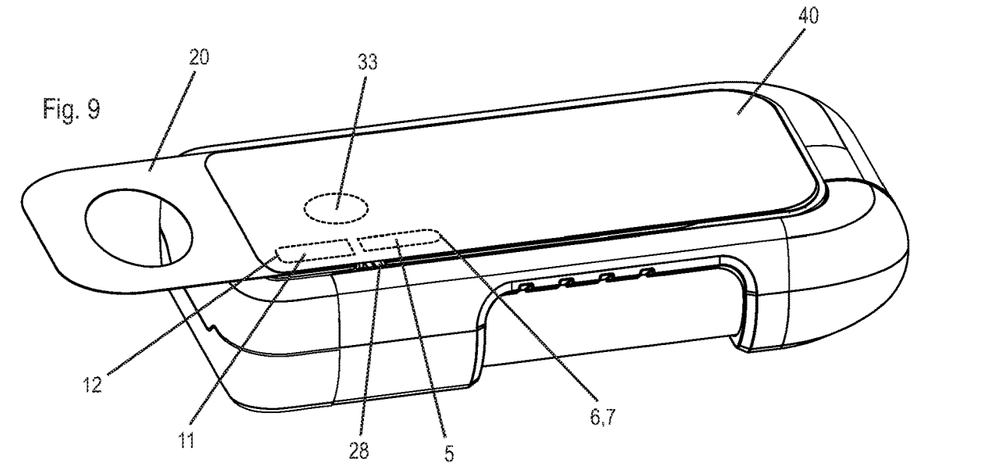
FIG. 9: Injection device whereby an additional strengthening sheet has been adhesively attached to the outside surface of the release liner thereby covering the ends of the sterile barrier films that are connected to the passage of the fluid path compartment and cartridge, respectively. Additionally, the strengthening sheet is attached to a third sterile barrier film covering the insertion needle.

A strengthening sheet (40) is attached to the release liner (20) to cover at least the end (6) of the first film (5), the end (12) of the second film (11), the third sterile film (33) and the aperture (28) of the release liner (FIG. 9). The strengthening sheet (40) may be adhesively attached to the surface of the release liner and the surfaces of the first and second films (5, 11) and the third sterile barrier film (33). The strengthening sheet (40) may be constructed from a polymeric material, a sheet of paper or from a woven or non-woven textile material. Examples for the polymeric sheet materials are: polyethylene terephthalate, polybutylene terephthalate, polyester foils, captam foils or polyolefin films such as high density polyethylene (HDPE) or polypropylene (PP) films. The strengthening sheet (40) strengthens the assembly of both sheets (20, 40), thereby preventing mechanical damage to the release liner (20) as the removal of the first and second films (5,11) from the inside of the housing (thereby releasing the connections between the first and second films (5,11) from the septum (3), aperture (25), respectively) may lead to stress concentrations around the aperture (28) in the release liner (20).

Figure 10:
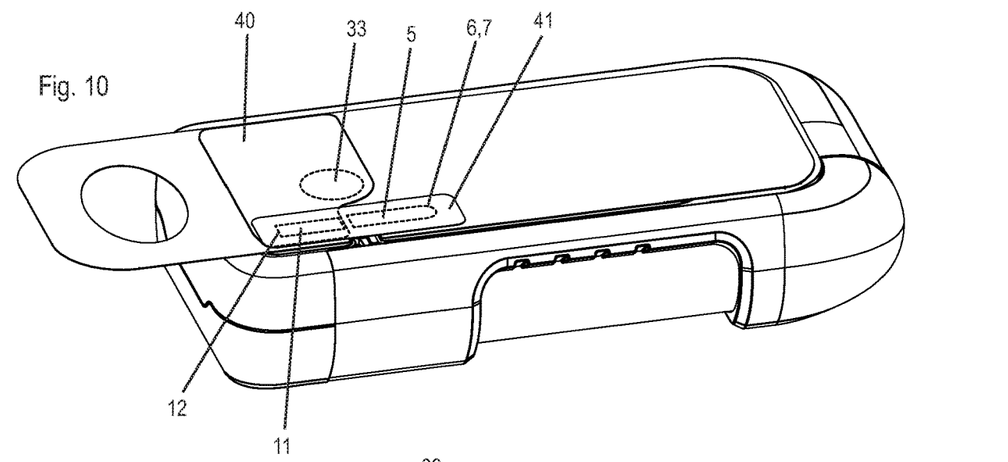
FIG. 10: Injection device with two strengthening sheets of material attached to the outside surface of the release liner, a first strengthening sheet covers the end of the second sterile barrier film that covers the passage of the fluid path compartment and the third sterile barrier film covering the insertion needle. The second strengthening sheet covers both ends of the first and second sterile barrier films.

A second embodiment is presented in FIG. 10, the second embodiment differs from the first embodiment in that the strengthening sheet (40) covers the third sterile barrier film (33), the second film (11) and the aperture (28) in the release liner. Thus the second film (11) with the second sterile barrier film (11a) connected to the compartment (13) enclosing the fluid path and the third barrier film (33) are first adhesively connected to the strengthening sheet (40) which may be followed by insertion of the cartridge (9) having the first film (5) connected thereto. The end of the first film (6) or the pull tab (10) may be attached to the release liner (20) after application of the strengthening sheet (40). A second strengthening sheet (41) may be finally applied to the first film (5) to strengthen the connection between the first film (5) and the release liner (20). The second strengthening sheet (41) may partially overlap with the strengthening sheet (40) as illustrated in FIG. 10.

Figure 11:
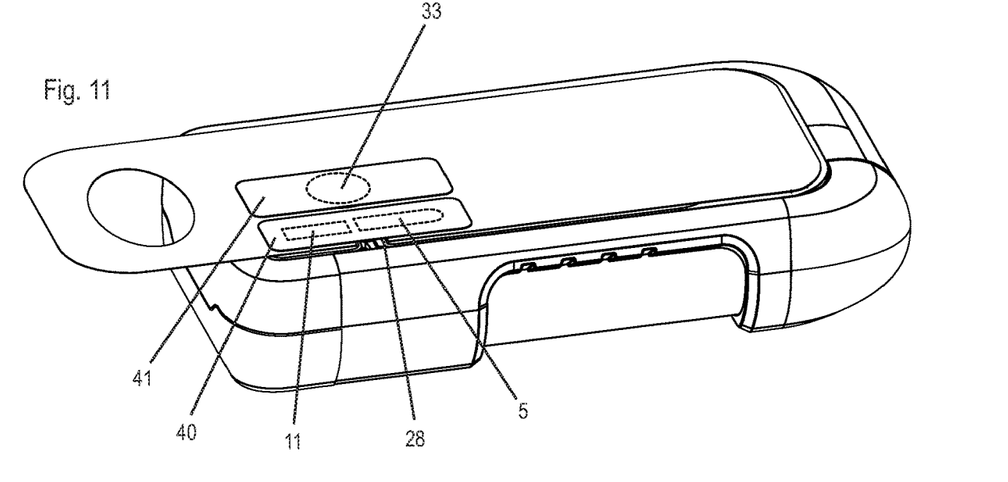
FIG. 11: Injection device with two strengthening sheets of material attached to the outside surface of the release liner, a first strengthening sheet covers both ends of the first and second sterile barrier film and a second strengthening sheet covers the third sterile barrier film.

A third embodiment is illustrated in FIG. 11. The strengthening sheet (40) is applied to the first and second films (5, 11) and covers the aperture (28). The second strengthening sheet (41) covers and adhesively connects to the third sterile barrier film (33).

Alternative embodiments can be easily derived based on the three embodiments described above. For example it can be envisioned that only the second film (11) is used in the device, maintaining the fluid path compartment (13) in a sterile condition whereas no first film (5) is used that covers the septum of the cartridge. Thus only the second film (11) and the third sterile barrier film (33) are covered by the strengthening sheet (40). Alternatively, only a first film (5) is used and no second film (11).

In yet another alternative, guide pulleys may be used within the device to guide the first film (5) and/or the second film (11) such that the forces required to remove the first and second barrier films (4, 11a) are reduced to facilitate the release liner (20) removal. Such a guide pulley system may be combined with the application of a strengthening sheet (40) to the release liner.

In yet another alternative, the injection device comprises a cartridge without a first sterile barrier film, whereas the fluid path compartment (13) is provided with a second film (11). The second film may be removed when the release liner is removed, but optionally the second film (11) is not removed and the fluid path needle (14) pierces the second sterile barrier film (11a) before piercing the septum of the cartridge upon device activation.

In yet another alternative, only a first film (5) is provided covering the septum of the cartridge whereas no second film (11) is applied to the housing of the fluid path compartment (13). The first film (5) may be removed upon removal of the release liner (20), but alternatively the needle may pierce through the first film (5) and the septum (27) when the first film is not removed.

In the claims, the word "comprising" does not exclude other elements or steps, and the indefinite article "a" or "an" does not exclude a plurality. For example "a first film" does not exclude the fact that there may be two films that functionally or structurally fulfill the purpose of "a first film". The mere fact that certain elements or steps are recited in distinct claims shall not preclude the existence of further meaningful combinations of these elements or steps.

| PART ANNOTATION | | | |
|---|---|---|---|
| 1 | Barrel | 19 | Ratchet counter member on housing |
| 2 | Neck | 20 | Release liner |
| 3 | Crimp | 21 | Skin adhesive |
| 4 | First sterile barrier film | 22 | First member |
| 5 | First film | 23 | Second member |
| 6 | End of first film | 24 | Aperture cartridge holder |
| 7 | Connector film | 25 | Passage fluid path compartment |
| 8 | U-shaped fold | 26 | Plunger |
| 9 | Cartridge | 27 | Septum |
| 10 | Pull tab | 28 | Aperture release liner |
| 11 | Second film | 29 | Cut out release liner |
| 11a | Second sterile barrier film | 30 | First adhesive spot |
| 12 | End of second film | 31 | Second adhesive spot |
| 13 | Compartment, housing of fluid path | 32 | Second aperture release liner |
| 14 | Needle, fluid path needle | 33 | Third sterile barrier film |
| 15 | Cartridge holder | 40 | Strengthening sheet |
| 16 | Injection device | 41 | Second strengthening sheet |
| 17 | External housing | 18, 19 | Ratchet system |
| 18 | Ratchet member | | |

What is claimed is:

1. An injection device configured for attachment to the skin of a patient using an adhesive layer, the injection device comprising:
   a housing having an adhesive layer;
   a first sterile barrier film within the housing;
   a film connected to the first sterile barrier film;
   a release liner covering the adhesive layer thereby preventing skin attachment, wherein the release liner comprises:
   a sheet of material with a first surface contacting the adhesive layer; and
   a first aperture configured for receiving said film connected to the first sterile barrier film located within the injection device, wherein an end of said film is connected to a second surface of the sheet of material that is opposite to the first surface; and
   a strengthening sheet connected to the second surface, the strengthening sheet covering at least a portion of the release liner and one or more of the first aperture and the end of the film.

2. The injection device according to claim 1, wherein the release liner further comprises a second aperture configured for receiving a hollow needle, wherein the second aperture is covered by a removable second sterile barrier film attached to the strengthening sheet.

3. The injection device according to claim 1, further comprising:
   a passage inside the housing;
   wherein the first sterile barrier film forms a removable sterile barrier covering said passage.

4. The injection device according to claim 3, further comprising:
   a sterile compartment including said passage, the sterile compartment enclosing a fluid path including a fluid path needle configured to be moved within the housing through said passage,
   wherein the first sterile barrier film maintains the sterile compartment in a sterile condition when covering the passage.

5. The injection device according to claim 4, wherein the first sterile barrier film forms a removable sterile barrier within the housing and maintains a surface within the housing in a sterile condition.

6. The injection device according claim 4, wherein:
   the strengthening sheet covers and connects to the end of the film of the first sterile barrier film,
   the strengthening sheet covers and connects to the end of the film of the first sterile barrier film covering a septum of a cartridge,
   or both.

7. The injection device according to claim 4, wherein the strengthening sheet covers and connects to a second film connected to a removable second sterile barrier film located within the injection device.

8. The injection device according to claim 4, wherein:
   the housing encloses the sterile compartment; and
   the fluid path needle is connected by a tube to a hollow needle.

9. The injection device according to claim 1, wherein:
   said film is an integral part of the first sterile barrier film, or
   said film is separate from and connected to the first sterile barrier film forming a pull tab for the first sterile barrier film.

10. The injection device according to claim 1, wherein the end of the film connected to the second surface of the sheet of material is adhesively connected or welded thereto.

11. The injection device according to claim 1, wherein the strengthening sheet is a first strengthening sheet, and further comprising:
   a second strengthening sheet attached to the second surface of the sheet of material of the release liner.

12. The injection device according to claim 11, wherein the second strengthening sheet covers and connects to a second film connected to a removable second sterile barrier film located within the injection device, a removable third sterile barrier film, or both.

13. The injection device according to claim 1, further comprising:
 a sensor;
 wherein the release liner comprises a conductive layer covering and electrically shielding the sensor.

14. The injection device according to claim 13, wherein the conductive layer comprises a silver ink layer, a carbon black layer, or both.

15. The injection device according to claim 1, wherein the housing comprises a cartridge holder for holding a cartridge comprising a fluid medicament sealed in a barrel by a moveable plunger and a septum.

16. The injection device according to claim 1, wherein the adhesive layer is connected to an outer surface of the housing.

17. The injection device according to claim 16, wherein the adhesive layer comprises one or more of: a skin adhesive layer for adhesion to the skin, a circuit layer comprising an electrically conductive sensor, or an adhesive layer for adhesion to the outer surface of the housing.

18. An injection device configured for attachment to the skin of a patient using an adhesive layer, the injection device comprising:
 a housing having an adhesive layer;
 a first sterile barrier film within the housing;
 a first film connected to the first sterile barrier film;
 a release liner covering the adhesive layer thereby preventing skin attachment, wherein the release liner comprises:
  a sheet of material with a first surface contacting the adhesive layer;
  an aperture defining a passage through which at least the first film passes,
  wherein the at least first film is connected to the first sterile barrier film and an end of the at least first film is connected to a second surface of the sheet of material that is opposite to the first surface; and
 a second sterile barrier film that is connected to the second surface of the sheet of material or that is located within the injection device and connected to a second film,
 wherein, when the second sterile barrier film is located within the injection device, an end of the second film extends through the aperture passage and is connected to the second surface of the sheet of material; and
 at least a first strengthening sheet connected to the second surface and covering the release liner, wherein the at least first strengthening sheet covers one or more features selected from the group consisting of: the aperture, the end of the at least first film, a portion of the second sterile barrier film located on the second surface of the sheet of material, and the end of the second film.

19. The injection device according to claim 18,
 wherein the second sterile barrier film is located within the injection device, and
 wherein the first sterile barrier film and the second sterile barrier film form removable sterile barriers within the injection device.

20. The injection device according to claim 19, further comprising:
 a second strengthening sheet attached to the second surface of the sheet of material, and
 wherein the second strengthening sheet covers at least another of the features not covered by the first strengthening sheet.

* * * * *